United States Patent
Drengler et al.

(10) Patent No.: US 7,923,210 B2
(45) Date of Patent: Apr. 12, 2011

(54) METHODS TO MEASURE IMMUNOSUPPRESSIVE TACROLIMUS, SIROLIMUS, AND CYCLOSPORIN A COMPLEXES IN A BLOOD SAMPLE

(75) Inventors: Susan M. Drengler, Lindenhurst, IL (US); Bennett W. Baugher, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/539,825

(22) Filed: Aug. 12, 2009

(65) Prior Publication Data

US 2009/0298090 A1 Dec. 3, 2009

Related U.S. Application Data

(62) Division of application No. 11/398,997, filed on Apr. 6, 2006, now Pat. No. 7,592,186.

(60) Provisional application No. 60/668,714, filed on Apr. 6, 2005.

(51) Int. Cl.
*G01N 33/53* (2006.01)
*G01N 1/00* (2006.01)
*A61K 49/00* (2006.01)

(52) U.S. Cl. ........ 435/7.1; 435/7.2; 435/7.23; 435/7.24; 435/7.25; 435/7.94; 436/517; 436/518; 436/522; 436/523; 436/538; 436/174; 436/177; 424/9.2

(58) Field of Classification Search .................. 435/7.1, 435/7.21, 7.23, 7.24, 7.8, 7.94, 7.2, 7.25; 436/506, 507, 517, 522, 523, 524, 528, 536, 436/538, 518, 174, 177; 514/11, 15; 530/321, 530/350, 363, 402; 424/9.2
See application file for complete search history.

(56) References Cited

U.S. PATENT DOCUMENTS

| | | | |
|---|---|---|---|
| 5,576,183 | A | 11/1996 | Kobayashi et al. |
| 5,756,301 | A | 5/1998 | Erlanger et al. |
| 5,811,525 | A | 9/1998 | Rittershaus |
| 5,936,070 | A | 8/1999 | Singh et al. |
| 6,338,946 | B1 * | 1/2002 | Kobayashi et al. ............ 435/7.1 |
| 6,613,739 | B1 * | 9/2003 | Naicker et al. .................. 514/11 |
| 2006/0014677 | A1 * | 1/2006 | Mayo .............................. 514/11 |

FOREIGN PATENT DOCUMENTS

EP 0750193 A1 12/1996

OTHER PUBLICATIONS

Abraham, et al., "Immunopharmacology of Rapamycin", Ann. Rev. Immunol., vol. 14, pp. 483-510, 1996.
Alak, A., "Measurement of Tacrolimus (FK506) and its Metabolites: A Review of Assay Development and application in Therapeutic Drug Monitoring and Pharmacokinetic Studies", Therap. Drug. Monit., vol. 19, pp. 338-351, 1997.
Armstrong, et al., "Modified pentamer formation assay for measurement of tacrolimus and its active metabolites: comparison with liquid chromatography-tandem mass spectrometry and microparticle enzyme-linked immunoassay (MEIA-II)", Clin. Chemistry, vol. 44, pp. 2516-2523, 1998.
Cardenas, et al., "Molecular mechanisms of immunosuppression by cyclosporine, FK506, and rapamycin", Current Opinion in Nephrology and Hypertension, vol. 4, No. 6, pp. 472-477, 1995.
Carreras, et al., An FKBP12 Binding Assay Based upon Biotinylated FKBP12, Analytical Biochemistry, vol. 298, Issue 1, pp. 57-61, Nov. 1, 2001.
Griffith, et al., "X-ray Structure of Calcineurin Inhibited by the Immunophilin-Immunosuppressant FKBP-12-FKB506 Complex", Cell, vol. 82, pp. 507-522, Aug. 11, 1995.
Kissinger, et al., "Crystal structures of human calcineurin and the human FKBP12-FK506-calcineurin complex", Nature, vol. 378, pp. 641-644, Dec. 7, 1995.
Mota, "Sirolimus: a new option in transplantation", Expert Opinion on Pharmacotherapy, vol. 6, No. 3, pp. 479-487, Mar. 2005.
Sabers, et al., "Isolation of Protein Target of the FKBP12-Rapamycin Complex in Mammalian Cells", The Journal of Biological Chemistry, vol. 270, No. 2, pp. 815-822, 1995.
PCT International Application No. PCT/US2006/012988, Search Report and Written Opinion of the International Searching Authority mailed Sep. 26, 2006.

* cited by examiner

*Primary Examiner* — Gailene R Gabel
(74) *Attorney, Agent, or Firm* — Audrey L. Bartnicki; Carol Larcher; Larcher & Chao Law Group

(57) ABSTRACT

The present invention provides methods, diagnostic assays, and diagnostic kits based on said methods, to determine levels of immunosuppressive complexes containing immunosuppressive drugs tacrolimus, sirolimus and cyclosporine A separately and in combination, formed in the blood of a drug-treated patient or in a patient candidate to immunosuppressive drug therapy. These methods, assays and kits are especially useful when using automated systems.

19 Claims, No Drawings

METHODS TO MEASURE IMMUNOSUPPRESSIVE TACROLIMUS, SIROLIMUS, AND CYCLOSPORIN A COMPLEXES IN A BLOOD SAMPLE

This application is a divisional of U.S. patent application Ser. No. 11/398,997, which was filed on Apr. 6, 2006, with a claim of priority to U.S. Provisional Patent Application No. 60/668,714 filed on Apr. 6, 2005, and which issued on Sep. 22, 2009, as U.S. Pat. No. 7,592,186.

FIELD OF THE INVENTION

The present invention relates to methods and diagnostic assays to determine the amounts of immunosuppressive complexes containing (individually or in combination) the immunosuppressive drugs tacrolimus, sirolimus or cyclosporine A in a blood sample.

BACKGROUND OF THE INVENTION

Cyclosporine A (CsA), tacrolimus (FK506, Prograf®) and sirolimus (rapamycin) are potent immunosuppressive drugs that inhibit T-lymphocyte proliferation. The action of these drugs is mediated through intracellular proteins called immunophilins. These immunophilins are rotamases (enzymes involved in protein folding).

Sirolimus and Tacrolimus share structural homology, and an inhibitory binding domain on a family of immunophilins, called FK506 binding proteins or FKBPs (Abraham et al., *Ann Rev. Immunol. Vol.* 14, 483 (1996)). Cyclosporin A binds to and inhibits cyclophilin, another immunophilin. In complex with the binding proteins these drugs inhibit secondary targets that regulate signal transduction pathways and result in inhibition of immune cell cycle progression. These pathways mediate and regulate the desired immunosuppression. These and other factors and pathways also systemically produce the undesirable drug effects through immune and other cell types.

Sirolimus and tacrolimus both interact with FKBP12, one member of the FKBP immunophilins, which is expressed in human blood. The dimers of sirolimus/FKBP12 and tacrolimus/FKBP12 complex with and inhibit separate target molecules. The Sirolimus/FKBP12 dimer target is called Mammalian Target of Rapamycin (mTOR). The Tacrolimus/FKBP12 dimer targets Calcineurin ((Abraham et al., (above); Chung et al., *Cell Vol.* 69, 1227 (1992)). The Cyclosporin A-cyclophilin dimer and tacrolimus/FKBP12 dimer separately can form a pentamer complex with and inhibit a common target, Calcineurin, a serine-threonine phosphatase.

Binding of the sirolimus/FKBP12 dimer to mTOR inhibits T-cell cell cycle progression. In T-cells Calcineurin/Calcium/Calmodulin bound to either tacrolimus/FKBP12 complex or the Cyclosporin A/cyclophilin complex prevents dephosphorylation of, and thus, reduces activation of several systemic signal transduction molecules, including NFAT which stimulates transcription of the immune modulator interleukin-2 (IL-2). The immunosuppressive effects of these drugs are achieved by the previously described multimeric complexes formed by these drugs with their binding proteins, their targets (enzymes that they inhibit), and other requisite cofactors. Tacrolimus has a narrow therapeutic range, because of this, monitoring of tacrolimus levels in patients undergoing tacrolimus immunosuppressive therapy is a standard practice. Current methods measure total (complexed and uncomplexed) drug concentration in blood. U.S. Pat. No. 6,338,946 relates to methods for manually assaying immunosuppressant drugs (with calcineurin-inhibiting activity) in vitro, i.e., by forming a complex of isolated tacrolimus with exogenous binding components immunosuppressant drug, specific immunophilin involved, bovine calcineurin, calmodulin, calcium), in a solid container and detecting the complex with an anti-calcineurin antibody tagged to a detection system. Other available methods extract tacrolimus from blood samples obtained from patients receiving tacrolimus, and measure the amount of extracted tacrolimus by forming in vitro complexes as described above ((Amstrong et al., *Clin. Chemistry Vol.* 44, pages 2516-2523 (1998)). These measurements are then compared to demographically determined drug toxicity concentration ranges and used to estimate potential toxic effects.

It has been demonstrated that there is a lack of correlation between total drug concentration and immunosuppression; therefore the measurement of total blood concentration of the drug is not predictive of individual immunosuppression responses. Variability in immunosuppressive drug response has been attributed to the discovery of several factors: inactive metabolites of the parent drugs that cross-react with the specific antibodies for the parent drugs in the assays, active metabolites of the parent drug that do not bind the assay antibody (and are not measured), and in great part to the fact that these assays measure total parent drug in a sample, rather than functional immune-suppressive complexes. It must be kept in mind that tacrolimus, sirolimus, and Cyclosporin A and their active metabolites act as immune-suppressants only when they form multimeric complexes with their particular binding immunophilins and target enzymes involved in immune cell suppression.

Each patient has different blood concentrations of these binding proteins and target components (due to age, gender, race, disease states, etc.). Thus, the ability to form immunosuppressive complexes and the number of complexes formed in the presence of each one of these drugs is uniquely (genetically, and/or environmentally) determined in each individual patient. Therefore, each patient has a unique degree of immune suppressive response, depending in part on the presence and abundance of the components required to form the immune-suppressive complexes.

When patients are treated with these hydrophobic immunosuppressive drugs, some of the drug is bound to functional binding proteins and affects immunosuppressive signal transduction pathways, but a significant fraction of drug is non-specifically bound to proteins, lipids, and membranes, becoming sequestered away from the immune cells where the immunosuppressive action takes place. Measuring total blood concentration of the immunosuppressive drug with currently available methods leads to an overestimation of the amount of functional drug present in blood because these methods measure functionally inactive drug as well drug involved in immunesuppression (Alak, A., *Therap. Drug, Monit., Vol.* 19, pages 338-351 (1997). Additionally, current methods that measure active metabolites of the parent drug lack correlation between their pharmacological activity and their immunologic cross-reactivities (Amstrong et al., *Clin. Chemistry Vol.* 44, pages 2516-2523 (1998)). It is also important to mention that current methods measuring total immunosuppressive drugs in a patient's blood sample are used to predict potential toxic effects, not to measure immunosuppressive therapeutic effects.

In view of the above, there is a need for assay methods that permit quantification of the functionally active immunosuppressive complexes, i.e. complexes formed in the patient's own blood. It is envisaged, without being bound to a theory, that through this quantification, an estimate of specific binding proteins and target components, and an estimate of potential immunosuppression before, or during, immunosuppressive therapy, will be provided. Specifically, in patients who had not started immunosuppressive therapy, quantification of the functionally active immunosuppressive complexes could help select the most appropriate drug treatment specific for each patient based on the patient's ability to form active complexes with tacrolimus, sirolimus or cyclosporine A, or combinations thereof, without subjecting the patient to unnecessary toxic drug effects caused by current trial and error drug selection methods. In patients already under immunosuppressive therapy, quantification of theoretical maximal immunosuppressive complexes may allow for a more reliable correlation between the pharmacologically active fraction of drug in blood and the immunosuppression observed in vivo in the patient. By adding saturating amounts of drug to a blood sample of a patient undergoing therapy and comparatively evaluating complexes formed in initial samples and in drug-saturated samples, information is obtained on the potential increase in immunosuppressive drug dosage that will result in increased immunosuppression without risking increased negative effects for the patient. Additionally, methods that permit measurement of the fraction of drug that forms functionally active immunosuppressive complexes can be adapted to allow a quantification of the proportions of complexes formed for each immunosuppressive drug when a patient is undergoing dual therapy.

All U.S. patents and publications referred to herein are hereby incorporated in their entirety by reference.

SUMMARY OF THE INVENTION

The present invention encompasses a method of measuring the amount of immune-suppressant complex components specific for an immunosuppressive drug present in a blood sample from an untreated patient in need of immunosuppressive therapy. This method comprises the steps of collecting the blood sample; lysing the blood cells; adding to the lysed blood cells an excess of the immune-suppressant drug to form drug-specific immune complexes; letting the complexes bind to a solid surface linked to an antibody specific for one of the blood components forming the complexes; adding an antibody conjugated with a detection marker, which is specific for one of the blood components forming the complexes, and which is not directly attached to the solid surface; and measuring the amount of the conjugated detection marker in the final mixture. The amount of detection marker will be proportional to the amount of immunosuppressive complex components present in said blood sample.

It should be noted that the present invention also encompasses the use of said method to select the most therapeutically effective immunosuppressive drug to be administered to an untreated patient in need thereof.

The present invention further encompasses a method of determining the maximum amount of immunosuppressive complexes formed by a specific immunosuppressive drug, which a patient under immunosuppressive therapy with the drug is able to form. This method comprises the steps of collecting the blood sample; lysing the blood cells in the sample; dividing the lysed blood cells in equal aliquots in two different containers; adding to the second of the two containers a volume of appropriate matrix with an excess of the same immunosuppressive drug being used in the treatment of the patient; adding to the first of the two containers the same volume of appropriate matrix as in the second container without the excess of immunosuppressive drug; letting the first and to the second container attach to equal solid surfaces tagged with an antibody specific for blood components that will form complexes with the immunosuppressive drug; washing each of both containers to remove unreacted components and interferents; adding to each of both containers an antibody tagged with a detection marker specific for the component forming said complex, and which is not bound to the solid surface's antibody; separately measuring the amount of detection marker in each of the two containers, wherein the amount of detection marker of the first container is proportional to the total number of complexes formed with the immunosuppressive drug, and the amount of detection marker of the second container is proportional to the theoretical maximal number of complexes that can be formed with additional immunosuppressive drug; and determining the difference between the amount of total actual complexes formed in first container with the amount of potential complexes that can be formed in second container. The difference represents the increase in immunosuppressive complexes that the patient under treatment with the immunosuppressive drug could potentially form.

It should be noted that the invention also encompasses the use of the method to predetermine the benefits of additional amount of currently administered immunosuppressive drug to a patient under treatment who is not achieving the required therapeutic effect.

The present invention further comprises a method of measuring the relative proportions of complexes formed by two immunosuppressive drugs, in a blood sample from a patient receiving dual drug treatment. This method comprises the steps of collecting said blood sample; lysing the blood cells; dividing the lysed cells in equal aliquots in two different containers; binding the lysed cells to a solid surface tagged with an antibody specific to blood components that are common to the two immunosuppressive drugs; adding to first container an antibody tagged to a detection marker specific for the immune complex being measured, which antibody is targeted to a different complex component than the solid surface-bound antibody; adding to second container a conjugated antibody tagged to a marker, specific for the immune complex being measured, which is targeted to a different complex component than the solid surface-bound antibody; and comparing the amounts of detection marker in first container and second containers to appropriate calibration curves to obtain relative proportions of complexes formed by each of the immunosuppressive drugs used in the dual drug treatment.

The present invention also encompasses the use of the method to determine the amount of immunosuppressive drug complex that is responsible for the therapeutic effect in drug combination therapies.

It should be noted that any of the methods of the present invention are applicable to immunosuppressive drugs selected from tacrolimus, sirolimus and cyclosporine A.

It should also be noted that the present invention encompasses diagnostic assays based on the methods of the present invention that are compatible with automated systems.

The present invention also encompasses kits comprising solid surfaces tagged with an antibody, and a different antibody tagged with a detection marker, wherein the antibodies are specific for different components of each of the complexes formed with the immunosuppressive drugs as disclosed above.

DETAILED DESCRIPTION OF THE PREFERRED EMBODIMENTS

The present invention relates to a method of measuring the relative amounts of immunosuppressive complex components, by determining the immunosuppressive complexes containing immunosuppressive drugs (or active metabolites of the drugs), namely, tacrolimus, sirolimus and cyclosporine A, in a blood sample, from (i) an untreated patient in need of immunosuppressive therapy, (ii) a patient already under treatment who is not achieving the intended immunosuppressive effect, and (iii) a patient who is receiving a drug combination therapy. The invention also relates to the use of these methods to determine: (i) the most beneficial immunosuppressive drug for therapy by determining the maximum amount of specific blood components present in a blood sample from a patient in need of immunosuppressive therapy, that will form complexes with a specific immunosuppressive drug before the beginning of the therapy; (ii) the potential benefit of increasing the amount of immunosuppressive drug already administered to a patient already under treatment with said immunosuppressive drug, when said patient is not reaching the intended immunosuppressive effect, and (iii) the relative proportions of immunosuppressive complexes due to each drug in patients undergoing dual drug therapy.

In a preferred embodiment of the present invention, the measurement of immunosuppressive complexes formed with each drug is used to estimate potential individual response to each drug before subjecting the patient to a specific therapy.

It is a well-known fact that each individual patient has different capacities to synthesize cellular components. Pharmacologically, only a small fraction of administered drug is bioavailable to work at the proper active site because of different mechanisms of sequestration or inactivation that take effect after a drug enters the blood stream. Drug toxicity occurs when a drug interacts with other tissues. Toxicity is potentiated when the drug saturates available sequestering moieties, causing rapid rise in free drug concentration in the blood. The lipophilic nature of these immunosuppressive drugs, their function as enzyme inhibitors and the abundant nature of the targets, make them central players in multiple signal transduction pathways. This dictates the delicacy of dose titration required to remain within a therapeutic window.

As a prelude to treatment, analysis of the patient's blood components, specific for each of the three drug candidates, namely tacrolimus, sirolimus and cyclosporine A, could be used to determine the maximal number of complexes that could be formed in the presence of each drug, using each of the assays specific for each drug. This information could be used to determine which signal transduction pathway components are more abundant in a patient, and suppression of which pathway (i.e. which drug) could give greatest benefit. This would avoid unnecessary toxicity by avoiding treatment with potentially less effective drug candidates.

Blood from a patient candidate to undergo immunosuppressive therapy can be collected in anticoagulant-treated containers, such as anticoagulant-treated tubes, to prevent clotting during collection. Anticoagulants that can be used with the present invention include, but are not limited to, EDTA and heparin. The use of EDTA may be contraindicated for Tacrolimus and Cyclosporin A because the formation of Calcineurin complexes is calcium-dependent. Thus, the anticoagulant-treated container can be an EDTA-free container.

A separation step to isolate white blood cells from red blood cells for analysis may be desirable because the immunosuppressive complexes of interest are in white blood cells. Separation would concentrate the cell type of interest, decreasing potential blood interferents in the sample and increasing assay sensitivity by increasing the concentration of drug complexes.

Mild detergents or some other means can be used to lyse white blood cells and release intact intracellular uncomplexed components from cells. Examples of mild detergents that can be used include, but are not limited to Triton X-100 and saponin. An excess of immunosuppressive drug is added to the cellular components in the appropriate matrix for a time and under conditions appropriate to form immunosuppressive complexes between the drug and the blood components. As used herein, matrix can be defined as the multiplicity of components forming the proper environment to form drug complexes with a solid surface and labeled antibodies having immunologic cross-reactivities with the isolated complexes; examples of said components are salts, buffers, preservatives, etc. Types of matrices for reaction, times and temperatures of incubation are known by the skilled in the art. The quantitative portion of the method begins by attachment to a solid surface of the passively formed immunosuppressive complexes through an antibody directed to either the binding protein or the target enzyme to which the drug is attached. Types of solid surfaces include but are not limited to microtiter plates, microparticles and coated test tubes.

The solid surface will allow holding of the complex attached to it during automated washing steps to remove inactive metabolites and interferents. After the washing steps, a labeled antibody directed to the side of the complex not directly attached to the solid surface (either the target protein or the target enzyme) is added and mixed, forming in this way the double antibody sandwich assay. The labeled antibody is ligated to a detection molecule that will permit quantification of the immunosuppressive complex trapped by the solid surface. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

The foundation for the isolation and quantification of the immunosuppressive complexes using double antibody "sandwich" assay technology is the high affinity of each immunosuppressive drug to specific blood proteins, and the high affinity of each of these complexes to their specific target proteins.

Sirolimus and tacrolimus share a binding domain on and the ability to inhibit FKBP12. Sirolimus bound to FKBP12 forms a complex with a target protein called Mammalian Target of Rapamycin (mTOR). Tacrolimus bound to FKBP12 targets Calcineurin, a serine/threonine phosphatase consisting of multiple subunits, Calcineurin A and Calcineurin B, Calmodulin and calcium.

Addition of aliquots of blood containing complexes of tacrolimus, calcineurin and FKBP12 to a solid surface-bound anti-Calcineurin A or B antibody attaches the immunosuppressive complexes to the solid surface. Addition of the labeled anti-FKBP12 would allow attachment of the detection molecules to the isolated complexes (in the case of Calcineurin-Cyclosporin A-cyclophilin complex the labeled antibody would be anti-cyclophilin). Using the same principle, an anti-mTOR antibody on the solid surface used with the anti-FKBP12 labeled antibody would create an assay for FKBP-Sirolimus-mTOR immune suppressive complexes.

To allow measurement of Tacrolimus and Cyclosporin A in the same sample the microparticle antibody would be anti-Calcineurin A or B, and the labeled antibodies would be anti-cyclophilin for CsA, and anti-FKBP12 for tacrolimus.

To allow measurement of Tacrolimus and Sirolimus in the same sample, the solid surface antibody could be anti-FKBP12, and the labeled antibodies would be anti-mTOR for Sirolimus, and Anti-Calcineurin A or B for Tacrolimus.

The present invention contemplates the use of a secondary goat anti-mouse monoclonal antibody covalently attached to the solid surface to allow addition of a primary, non-covalent mouse antibody to produce a solid surface with antibody that is specific for the antigen of interest (immunophilin of choice or target of choice). This method may result in increased signal to background ratio in the assay.

The interaction between immune complex, solid surface and labeled antibodies can be performed simultaneously (in one step), or sequentially (in two steps) with washing between addition of the sample to the solid surface and addition of the labeled antibody.

Addition of reagents to produce signal in proportion to the amount of labeled antibody bound allows detection and quantification.

Detection molecules may be any of those that produce a signal that is quantifiable. Signal-generating molecules can include, but are not limited to alkaline phosphatase, luminol, horseradish peroxidase, fluorescein, acridinium and radiolabel bound to appropriate antibodies.

Complexes can be quantified by comparing to calibrators and controls. Calibrators and controls consist, for example for tacrolimus determination, of known levels of tacrolimus titrated into a cocktail of purified Calcineurin A & B, calmodulin, FKBP12, calcium, buffer at a defined pH, (possibly in a detergent to mimic the sample binding environment) to form complexes for calibration.

Examples illustrating the different components of the assays for the determination of complexes formed with the immunosuppressive drugs tacrolimus, sirolimus and cyclosporine A are presented in the table below.

| Drug | Enzyme Binding Protein | Enzyme Target | Requisite Cofactors | Solid Surface Antibody Options | Labeled Antibody Options |
|---|---|---|---|---|---|
| Tacrolimus | FKBP12 | Calcineurin A (CaN A) Calcineurin B (CaN B) | Calmodulin $Calcium^{2+}$ | Anti-FKBP12 Anti-CaN A Anti-CaN B | Anti-FKBP12 Anti-CaN A Anti-CaN B |
| Sirolimus | FKBP12 | mTOR | | Anti-FKBP12 Anti-mTOR | Anti-FKBP12 Anti-mTOR |
| Cyclosporin A | cyclophilin | Calcineurin A Calcineurin B | Calmodulin $Calcium^{2+}$ | Anti-CaN A Anti-CaN B Anti-Cyclophillin | Anti-CaN A Anti-CaN B Anti-Cyclophillin |

It is important to remember that the same antibody may not be both the labeled and the solid surface antibody because two unique epitopes are required to attach both the solid surface and the labeled antibodies to the immunosuppressive complex.

It should be noted that the method described can be practiced by using manual or automated means. By automated means it is intended a technical device designed to analyze and measure components from biological fluids with increased efficiency.

Although the above-preferred embodiment is illustrated by reference to the detection of blood immunosuppressive complexes in naïve blood from patients that are not under immunosuppressive therapy, the present invention can be used to measure how much immunosuppressive complex of a specific immunosuppressive drug is formed in patients already undergoing treatment with said drug. In addition, the same blood sample could be divided and one portion treated to a saturating concentration of drug to predict how much immunosuppressive complex the patient can potentially form with intrinsic, available components.

This is particularly important when a patient undergoing therapy is not able to achieve the desired immunosuppressive effect. Measuring the theoretically maximal amount of complexes that can be formed will help discriminate between an insufficient dosage or a lack of specific blood components that will form immune complexes required to produce an immunosuppressive response.

Blood samples can be obtained from a patient undergoing immunosuppressive therapy with any of the drugs tacrolimus, sirolimus or cyclosporine A as described above. Part of the sample will be incubated with an excess of the immunosuppressive drug being used in the therapy dissolved in the appropriate matrix and the complexes determined as described above, using a specific antibody bound to a solid surface, and an antibody tagged to a detection marker. An appropriate matrix to solubilize these hydrophobic drugs would include organic solvents or aqueous buffers containing carrier proteins. This will allow a significant fraction of the uncomplexed components currently available, to form complexes to be measured as the "theoretical maximal number of complexes". The other part of the sample will be incubated in the appropriate matrix without the excess of the immunosuppressive drug being used in the appropriate matrix and the complexes determined as described above. This will measure the complexes formed during therapy (and already present in the patient's blood sample) i.e., "total number of complexes". Analysis of the "theoretical maximal number of complexes" and comparisons with the "total number of complexes", would allow determination of the "percentage of theoretical maximal complexes", individualized for each patient. A range of therapeutic benefit could be established.

Complexes would be determined by comparing to a calibration curve and comparing concentrations derived from the calibrations.

It will be appreciated that this method can be used to select additional amount of immunosuppressive drug to be administered to a patient under treatment who has insufficient immunosuppressive effect, wherein the immunosuppressive drug is selected form the group consisting of tacrolimus, sirolimus and cyclosporine A.

In another embodiment of the present invention the method described above can be used in patients undergoing dual drug therapy. It will be appreciated that these methods and assays could measure the proportional amounts of immunosuppressive complex formed by each drug. The immune complexes containing the two drugs of interest could be measured in separate assays after complex isolation described above. The measurement of two types of complexes would require the antibody bound to the solid surface be one the two drugs have in common. After binding two samples to the solid surface and washing, the specific labeled antibodies would be added and results compared to separate calibrations for each type of complex. When compared to prepared calibrators, a proportionate estimate of the two drugs in the same sample can be obtained.

The present invention also encompasses diagnostic assays based on the methods described above to be used in automated systems. This will overcome labor-intensity and expense of manual assays, and at the same time permits a larger number of samples to be assayed in a given time. Solid surfaces applicable to automated systems include, but are not limited to microparticles. Automated systems include but are not limited to for example IMx® System, Architect i2000, and Architect i8000.

Another embodiment of the present invention also comprises diagnostic kits comprising antibodies directed to each target enzyme or target protein specific for each of the immunosuppressive drugs disclosed in the description, in which kit, the one antibody will be attached to a solid surface and the other antibody will be tagged to a detection marker.

The present invention will now be illustrated by means of examples of assays for the determination of one drug in particular or for two or more drugs administered simultaneously. The examples should not be construed as imposing any limitation on the scope of the claims.

EXAMPLE I

| Assay | Isolation of ligand | Solid Surface Antibody | Isolated complex (ligand) | Labeled Antibody |
|---|---|---|---|---|
| Tacrolimus (FK506) | Buffered detergent and/or organic solvent mixture | anti-Calcineurin B (CnB) antibody | Calcineurin/FK506/ FKBP12 | anti-FKBP12 antibody |
| Cyclosporine A (CsA) | Buffered detergent and/or organic solvent mixture | anti-Calcineurin B antibody | Calcineurin/CsA/ Cyclophilin | anti-Cyclophilin antibody |
| Sirolimus (rapamycin) | Buffered detergent and/or organic solvent mixture | anti-mTOR antibody | mTOR/rapamycin/ FKBP12 | anti-FKBP12 antibody |

EXAMPLE II

| Assay combination | Isolation of ligand | Solid Surface Antibody | Isolated complex (ligand) | Conjugate Antibodies |
|---|---|---|---|---|
| Tacro & Sirolimus | mild detergent and/or organic solvent mixture | anti-FKBP12 antibody | FKBP12/rapamycin/ mTOR and FKBP12/FK506/ Calcineurin | 1) anti-mTOR antibody 2) anti-Calcineurin B antibody |
| Tacro & CsA | mild detergent and/or organic solvent mixture | anti-Calcineurin A or B antibody | Calcineurin/FK506/ FKBP12 and Calcineurin/CsA/ Cyclophilin | 1) anti-Cyclophilin antibody 2) anti-FKBP12 |

What is claimed is:

1. A method of measuring the amount of immunosuppressive complex components, which are specific for an immunosuppressive drug, that are present in a blood sample from an untreated patient in need of immunosuppressive therapy using the immunosuppressive drug, which method comprises the steps of:
   a) lysing a sample of blood obtained from the patient to obtain blood components;
   b) adding to the lysed sample of blood an excess of the immunosuppressive drug to form drug-specific immune complexes;
   c) contacting the mixture of step (b) with a solid surface to which is linked a first antibody, which is specific for an epitope on a blood component in immunosuppressive complex with the immunosuppressant drug, whereupon the immunosuppressive complex is bound by the first antibody linked to the solid surface;
   d) washing to remove any uncomplexed blood components;
   e) contacting immunosuppressive complex bound by the first antibody linked to the solid surface with a second antibody, which is labeled with a detection molecule and which is specific for another epitope on a blood component, which can be the same blood component bound by the first antibody in step (c) or a different blood component in immunosuppressive complex with the immunosuppressant drug, whereupon the immunosuppressive complex is bound by the second antibody;
   f) washing to remove any unbound second antibody; and
   g) measuring the amount of detection molecule on the second antibody, which bound to the immunosuppressive complex that was bound by the first antibody in the mixture of step (e), wherein the amount of detection molecule is proportional to the amount of immunosuppressive complex components present in said blood sample that will bind and form immunosuppressive complexes with the immunosuppressive drug.

2. The method of claim 1, wherein the blood sample was collected in an anticoagulant-treated container.

3. The method of claim 2, wherein the anticoagulant-treated container is an ethylenediaminetetraacetic acid (EDTA)-free container.

4. The method of claim 1, wherein red blood cells are separated away from the sample of blood before lysing the sample of blood.

5. The method of claim 1, wherein steps (c)-(g) of the method are achieved using automated means.

6. The method of claim 5, wherein the solid surface comprises microparticles.

7. The method of claim 6, wherein the immunosuppressant drug is Tacrolimus.

8. The method of claim 7 wherein:
   the first antibody bound to the microparticles of step (c) is selected from the group consisting of anti-FKBP12 antibody and anti-Calcineurin A or B antibody;
   the second antibody labeled with a detection molecule of step (e) is selected from the group of anti-FKBP12 antibody and anti-Calcineurin A or B antibody; and
   the detection molecule of step (e) is selected from the group consisting of acridinium, luminol, horseradish peroxidase, fluorescein, alkaline phosphatase and a radioisotope.

9. The method of claim 8, wherein the first antibody bound to the microparticles further comprises goat anti-mouse antibody and mouse anti-FKBP antibody.

10. The method of claim 8, wherein the first antibody bound to the microparticles further comprises goat anti-mouse antibody and mouse anti-Calcineurin A or B antibodies.

11. The method of claim 6, wherein the immunosuppressant drug is sirolimus.

12. The method of claim 11, wherein:
the first antibody bound to the microparticles of step (c) is selected from the group of anti-FKBP12 antibody and anti-mTOR antibody;
the second antibody labeled with a detection molecule of step (e) is selected from the group of anti-FKBP12 antibody and anti-mTOR antibody; and
the detection molecule of step (e) is selected from the group consisting of acridinium, luminol, horseradish peroxidase, fluorescein, alkaline phosphatase and a radioisotope.

13. The method of claim 12, wherein the first antibody bound to the microparticles further comprises goat anti-mouse antibody and mouse anti-FKBP antibody.

14. The method of claim 12, wherein the first antibody bound to the microparticles further comprises goat anti-mouse antibody and mouse anti-mTOR antibody.

15. The method of claim 6, wherein the immunosuppressant drug is cyclosporine A.

16. The method of claim 15, wherein:
the first antibody bound to the microparticles of step (c) is selected from the group consisting of anti-cyclophilin antibody and anti-Calcineurin antibody;
the second antibody labeled with a detection molecule of step (e) is selected from the group of anti-cyclophilin antibody and anti-Calcineurin antibody; and
the detection molecule of step (e) is selected from the group consisting of acridinium, luminol, horseradish peroxidase, fluorescein, alkaline phosphatase and a radioisotope.

17. The method of claim 16, wherein the first antibody bound to the microparticles further comprises goat anti-mouse antibody and mouse anti-cyclophilin antibody.

18. The method of claim 16, wherein the first antibody bound to the microparticles further comprises goat anti-mouse antibody and mouse anti-Calcineurin A or B antibody.

19. The method of claim 1, which further comprises identifying an immunosuppressant drug selected from the group consisting of tacrolimus, sirolimus, and cyclosporine A that could be administered to an untreated patient in need of immunosuppressive therapy based on the amount of immunosuppressive complex components present in said blood sample that formed immunosuppressive complexes with the immunosuppressant drug.

* * * * *